United States Patent [19]

Chassaing et al.

[11] Patent Number: 5,475,145
[45] Date of Patent: Dec. 12, 1995

[54] β-DIKETONES, PROCESSES FOR MAKING β-DIKETONES AND USE OF β-DIKETONES AS STABILIZERS FOR PVC

[75] Inventors: Serge Chassaing, Melle; Michel Gay, Villeurbanne; Gilles Mur, Saint-Maur des Fosses, all of France

[73] Assignee: Rhone-Poulenc, Courbevoie, France

[21] Appl. No.: 148,256

[22] Filed: Nov. 5, 1993

[30] Foreign Application Priority Data

Nov. 6, 1992 [FR] France .................................. 92 13366
Feb. 1, 1993 [FR] France .................................. 93 01025

[51] Int. Cl.$^6$ .................................................. C07C 49/76
[52] U.S. Cl. .......................... 568/335; 568/412; 568/413; 568/331; 568/336
[58] Field of Search ................................... 568/331, 412, 568/413, 335, 336

[56] References Cited

U.S. PATENT DOCUMENTS

| | | | |
|---|---|---|---|
| 2,313,621 | 6/1947 | Bruson | 568/412 |
| 2,432,499 | 12/1947 | Boese | 568/331 |
| 3,047,375 | 7/1962 | Pellegrini | 568/412 |
| 3,406,220 | 10/1968 | Hawkins | 568/331 |
| 3,994,869 | 11/1976 | Gontarz et al. | 358/413 |
| 4,235,823 | 11/1980 | Dudick et al. | 568/412 |
| 4,387,089 | 6/1983 | De Pole | 568/331 |
| 4,590,233 | 5/1986 | Erwied et al. | 568/413 |
| 4,739,104 | 4/1988 | Werner et al. | 568/413 |
| 4,992,504 | 2/1991 | Wirth et al. | 568/413 |
| 5,015,777 | 5/1991 | Chisolm et al. | 568/413 |
| 5,071,898 | 12/1991 | Wirth et al. | 568/413 |

FOREIGN PATENT DOCUMENTS

| | | |
|---|---|---|
| 028758 | 10/1980 | European Pat. Off. . |
| 062813 | 3/1982 | European Pat. Off. . |
| 0114607 | 8/1984 | European Pat. Off. ............... 568/413 |
| 0416564A2 | 3/1991 | European Pat. Off. ............... 568/413 |
| 507013 | 4/1991 | European Pat. Off. . |
| 2165836 | 5/1972 | France . |

OTHER PUBLICATIONS

6060 European Polymer Journal, Stabilization of Poly(Vinyl Chloride) by –Dicarbony Compounds, Marsh Barton, 25(1989), No. 12, pp. 1245–1250.
Chemical Abstracts No. 774346, vol. 92, No. 10 (1980).
Chemical Abstracts No. 59367, vol. 118, No. 7 (1993).
Chemical Abstracts No. 93760d, vol. 115, No. 10 (1991).
Chemical Abstracts No. 268323p, vol. 116, No. 26 (1982).

*Primary Examiner*—James H. Reamer
*Attorney, Agent, or Firm*—Finnegan, Henderson, Farabow, Garrett & Dunner

[57]  ABSTRACT

The present invention is directed to compositions containing novel beta-diketones of formula (I) and formula (II), $$R_1COCH_2COR_2 \qquad (I)$$

$$R_2COCH_2COR_2 \qquad (II)$$

which may be used to stabilize various polymers, such as polyvinyl chlorides (PVCs). The present invention is also directed to a method for preparing β-diketones by a Claisen condensation reaction, which is represented as follows:

$$R_4COCHR_5H + R_6C(O)OR_7 + RO^- \rightarrow [R_4COCR_5COR_6]^- + R_7OH + ROH.$$

11 Claims, No Drawings

β-DIKETONES, PROCESSES FOR MAKING β-DIKETONES AND USE OF β-DIKETONES AS STABILIZERS FOR PVC

The present invention is directed to compositions containing novel beta-diketones of formula (I) and formula (II), $$R_1COCH_2COR_2 \qquad (I)$$

$$R_2COCH_2COR_2 \qquad (II)$$

which may be used to stabilize various polymers, such as polyvinyl chlorides (PVCs). The present invention is also directed to a method for preparing β-diketones by a Claisen condensation reaction, which is represented as follows:

$$R_4COCHR_5H + R_6C(O)OR_7 + RO^- \rightarrow [R_4COCR_5COR_6] \rightarrow R_7OH + ROH.$$

β-Diketones are a class of compounds which enjoy wide commercial application, such as in metal extraction and stabilization of polymers. β-Diketones are today the best readily available organic stabilizers for halogenated polymers, such as PVC. Accordingly, these compounds have become increasingly important commercially.

Development of stabilizing compositions has not, however, produced compositions containing β-diketones which are soluble in and/or serve as the solvent for other additives in the stabilizing composition. Commercial demand is increasing for liquid stabilizing compositions for halogenated polymers which are "all-in-one" or "one-pack" formulations, and which do not produce an unpleasant odor. Up to the present time, additional solvents have been used to formulate liquid stabilizing compositions, but the use of such solvents has become increasingly inadvisable, primarily due to concerns for occupational health and the problem of removing volatile elements present in the stabilized polymer.

Accordingly, there is a need for a β-diketone composition which is not only liquid at the temperature at which it is used (generally ambient temperature), but also is miscible, even in large proportions, with other ingredients of an "all-in-one" liquid stabilizing formulation for halogenated polymers.

The advantages of a low-viscosity liquid product are considerable—the following is a non-exhaustive list:

- the product can be metered and injected by pump into the polymer mass;
- the product may be impregnated in a support such as hydrotalcite mineral, $CaCO_3$, and salts of Ca and Zn; and
- one may use a "dustless" operation, which provides an important advantage in non-food applications over dibenzoylmethane, which has quite low explosive limits.

The cost of manufacture, however, has been a primary concern in the development of β-diketones, as it is quite impractical, for example, to employ expensive stabilizing agents in the polymer industry.

Presently, the most common method employed to prepare β-diketones is the reaction of an ester with a carbanion of a ketone, which is disclosed in European Patent No. 0,454,623 (Ciba-Geigy AG) and U.S. Pat. No. 5,015,777 (Witco). This method, however, can disadvantageously lead to an abundance of side-reactions, such as crotonization and formation of β-ketoesters.

For example, in European Patent No. 0,454,623, attempts were made to improve the yield of β-diketones using dimethyl sulfoxide (DMSO), a costly solvent, possibly with the addition of alcohol, at a low temperature and in the presence of sodium hydroxide or an alcoholate. Yields in relation to the ester, however, can be mediocre.

Similarly, in U.S. Pat. No. 5,015,777, the solvents used are less expensive and more easily separated from the crude reaction mixture, but a large excess of ester is used. After removal of the alkyl benzoates, the yield with respect to the ester can be mediocre to poor. Moreover, poor reaction yields lead to a reaction mixture that cannot be used without a highly effective purification, and the large excess of ester requires recycling, which is often costly and otherwise undesirable.

Accordingly, it is an object of the invention to devise a stabilizing composition containing a β-diketone which is liquid at the temperature at which the composition is used. It is also an object of the invention to provide a stabilizing composition containing a β-diketone which is at least partially miscible with other ingredients of an "all-in-one" liquid stabilizing formulation.

It is also an object of the present invention to provide a method that makes it possible to obtain excellent yields of β-diketones, while using inexpensive reagents. It is a further object of the present invention to provide a method that makes it possible to obtain β-diketones of high purity.

In accordance with these and other objects, a first embodiment of the present invention is directed to a stabilizing composition for halogenated polymers which comprises an effective amount of at least one β-diketone compound represented by formula (I):

$$R_1COCH_2COR_2 \qquad (I)$$

or formula (II)

$$R_2COCH_2COR_2 \qquad (II)$$

in which $R_1$ is represented by the formula $$(Y)_n\text{-}\Phi\text{-},$$

wherein $\Phi$ is phenyl and each Y, which may be the same or different, is a hydrogen atom or a group selected from hydrocarbon chains having 1 to 12 carbon atoms, alkoxys, silyls and nonreactive halogen atoms; each $R_2$, which may be the same or different, represents a hydrogen atom or a group selected from hydrocarbon chains having 1 or 5 to 12 carbon atoms, which may be interrupted by one or more oxygen atoms, aralkyls, alkoxys and silyls; and n represents an integer from 0 to 3; with the proviso that if the number of carbon atoms in $R_2$ in formula (I) is less than 5, the sum of the carbons contained in Y is at least 3 and at most 12, and that in formula (II) the total number of carbon atoms in the two $R_2$s is at least 10.

A second embodiment of the present invention is directed to a method for preparing β-diketones of the formula $$R_4COCHR_5COR_6$$

by the reaction of a ketone of the formula $R_4COCHR_5H$ with an ester of the formula $R_6C(O)OR_7$, in the presence of an alcoholate of which the alcohol is volatile under the conditions of operation, wherein $R_4$ and $R_6$, which may be the same or different, each represents a hydrocarbon group which may be substituted and may optionally be linked to form a cyclic compound and $R_5$ is a hydrogen or a hydrocarbon group; and $R_7$ represents a hydrocarbon group such that the alcohol $R_7OH$ is volatile under the reaction conditions.

A third embodiment of the invention is directed to β-diketones formed according to the process described above.

A fourth embodiment of the invention is directed to halogenated polymers, in particular PVC, containing the β-diketone stabilizing composition of the present invention.

The present invention is directed to a stabilizing composition for halogenated polymers, such as PVC. The stabilizing composition comprises an effective amount of at least one β-diketone compound represented by formula (I):

$$R_1COCH_2COR_2 \qquad (I)$$

or formula (II)

$$R_2COCH_2COR_2 \qquad (II)$$

in which $R_1$ is represented by the formula $$(Y)_n\text{-}\Phi\text{-},$$

in which Φ is phenyl and each Y, which may be the same or different, is a hydrogen atom or a group selected from
non-cyclic hydrocarbon chains having 1 to 12 carbon atoms, alkoxy, silyl, and
nonreactive halogen atoms;
each $R_2$, which may be the same or different, represents a hydrogen atom or a group selected from
non-cyclic hydrocarbon chains having 1 or 5 to 12 carbon atoms, which are optionally interrupted by at least one oxygen atom, aralkyls, alkoxys, or silyls; and
n represents an integer from 0 to 3, preferably 0 or 1, with the proviso that if the number of carbon atoms in $R_2$ in formula (I) is less than 5, the sum of the carbons contained in the Y groups is at least 3 and at most 12, and that in formula (II), the total number of the carbon atoms in the two $R_2$s is at least 10.

Preferably, Y is an alkyl group having from 1 to 12 carbon atoms. Preferably, the sum of the number of carbon atoms in the Y groups is less than 6. More preferably, the sum of the number of carbon atoms is 3. Advantageously, the sum of the number of carbon atoms in the radical groups Y and those in $R_2$ is less than 12, preferably 10.

It is also preferable that one of the Y's, or the only Y, is in the para position with respect to the β-diketone chain.

Preferably, if the hydrocarbon chain is linear, the number of carbon atoms in $R_2$ is preferably between 5 and 9, more preferably between 5 and 7. If the hydrocarbon chain is branched, the number of carbon atoms in $R_2$ is preferably between 5 and 12, more preferably between 5 and 9. Preferably, if the hydrocarbon chain is interrupted by more than one oxygen atom, each oxygen atom is preferably separated from the other by at least 2 carbon atoms, as in the glymes.

The amount of β-diketone compounds to be employed in the stabilizing composition can readily be determined by one of skill in the art. Preferably, the stabilizing composition comprises (on a molar basis) at least ⅔ of the β-diketone compounds, more preferably ¾, and most preferably ⅘. Preferably, the major constituent of the stabilizing composition is the β-diketone which is represented by formula (I).

It is preferred that, in addition to the β-diketone compound represented by formula (I) or (II) which is the major constituent of the stabilizing composition, the composition further comprises at least one other β-diketone compound of formula (I), formula (II), and/or formula (III)

$$R_1COCH_2COR_1 \qquad (III)$$

wherein each $R_1$, which may be the same or different, has the same meaning as described above.

It is particularly preferred that the total amount of the at least one other β-diketone compound of formulae (I), (II), and/or (III), added to the polymer in addition to the major constituent, is at least 5% of the amount of the major constituent. More preferably, the total amount of the other β-diketone compounds is at least 10% of the amount of the major constituent, most preferably at least 15%. The amounts of each of the other β-diketone compounds may be determined by the skilled worker. Preferably, the sum of the amounts of compounds of formula (III) is not more than 10% of the sum of the amounts of compounds of formulae (I) and (II).

Generally, toxicity increases or decreases linearly with the number of carbon atoms in the compound. Unexpectedly, the toxicity of the inventive β-diketone compositions is surprisingly low and can be too low to be measured. Certain β-diketones, which are not a part of the present invention, have a toxicity which is non-negligible but low. For example, isovalerylbenzoylmethane has an acute toxicity $LD_{50}$ per os in the rat of 4885 mg/kg. In sharp contrast, the toxicity of the β-diketone compounds according to the present invention can be so low as to be not measurable. For the compounds where $R_1$ is phenyl and $R_2$ is a linear group, particularly $C_7$, the $LD_{50}$ is generally greater than 5000 mg/kg (rat, p.o.).

In addition, under operating conditions in PVC, the β-diketone compositions according to the present invention can release substantially no odor, in sharp contrast to closely related compounds. This is, in fact, quite remarkable because certain lower homologs, such as the product where $R_1$ is phenyl and $R_2$ is $C_4$ ($R_2=(CH_3)_2CHCH_2$—), display an intolerable odor when degradation occurs either during storage of the composition or during transformation of the PVC.

Furthermore, contrary to prevailing opinion among those skilled in the art that the presence, as a stabilizer, of di-aromatic β-diketones, such as dibenzoylmethane, gives rise to intense coloration in the presence of iron (probably due to strong absorption of a chelate in the 400–450 nm range of wavelengths), the compositions according to the present invention may contain relatively high proportions of di-aromatic diketones without displaying color intensification.

The β-diketone employed in the stabilizing composition should preferably be liquid at a temperature of 50° C. More preferably, the β-diketone is liquid at a temperature of 30° C.; most preferably at 0° C. Particularly preferred β-diketones are those which are liquid at ambient temperature.

When employed as a homogeneous liquid additive for PVC, the stabilizing composition comprising a β-diketone compound of formula (I) and/or (II) described above preferably further comprises at least one accompanying compound selected from, inter alia, the salts of zinc, the salts of alkaline earth metals, and the organic phosphites. One of skill in the art can readily select suitable accompanying compounds for inclusion in the inventive stabilizing composition. Examples of such compounds include zinc propionate, zinc 2-ethylhexanoate, zinc laurate, zinc stearate, zinc oleate, zinc ricinoleate, zinc docosanoate, zinc benzoate, zinc para-tert-butylbenzoate, zinc salicylate, zinc mono(2-ethylhexyl) maleate, zinc nonylphenates, and salts of calcium and magnesium barium with maleic, acetic, diacetic, propionic, hexanoic, 2-ethylhexanoic, decanoic, undecanoic, lauric, myristic, palmitic, stearic, oleic, ricinoleic, behenic (docosanoic), hydroxystearic, hydroxyundecanoic, benzoic, phenylacetic, para-tert-butylbenzoic and salicylic acids, and the calcium and magnesium phenolates from phenol and phenols substituted by one or more alkyl radicals, such as nonylphenols.

Preferably, the ratio between the sum of the β-diketone compounds and the amount of said accompanying compound is at least 1:100. More preferably, the ratio is 1:50; most preferably 1:20.

The present invention is also directed to a method for the synthesis of β-diketones of the formula $$R_4COCHR_5COR_6$$

by reaction of a ketone of the formula $R_4COCHR_5H$ with an ester of the formula $R_6C(O)OR_7$, in the presence of an alcoholate of which the alcohol is volatile under the conditions of operation,
in which $R_4$ and $R_6$, which may be the same or different, each represent a hydrocarbon group and may optionally be linked to form a cyclic compound;

$R_5$ is a hydrogen atom or a hydrocarbon group; and $R_7$ is a hydrocarbon group, such that the alcohol $R_7OH$ is volatile under the reaction conditions.

Preferably, $R_4$ and $R_6$ are a hydrocarbon group having from 1 to 30 carbon atoms, more preferably from 1 to 18 carbon atoms. Most preferably, $R_4$ and $R_6$ are selected from alkyl or alkenyl, linear or branched, having from 1 to 24 carbon atoms; aralkyl having 7 to 10 carbon atoms; and aryl or cycloaliphatic, which may have one or more double bonds, each having less than 14 carbon atoms. $R_4$ and $R_6$ may optionally be substituted, for example, by halogen atoms or alkyl groups, such as methyl and ethyl and may contain one or more of —O—, —CO—O—, —CO—, and Si in the aliphatic chain. Alternatively, $R_4$ and $R_6$ may together form a divalent group having 2 to 5 carbon atoms, optionally containing a hetero atom, such as oxygen or nitrogen.

Preferably, $R_5$ is a hydrogen atom or an alkyl group having 1 to 4 carbon atoms, which may be substituted or unsubstituted, and may contain one or more of —O—, —CO—O—, and —CO—. More preferably, $R_5$ is a hydrogen atom.

Preferably, $R_7$ is an alkyl group having 1 to 4 carbon atoms. More preferably, $R_7$ is a methyl group.

According to a preferred embodiment of the present invention, a reaction mixture is provided that contains the alcoholate, the ester and a solvent. To this mixture is added the ketone, while progressively removing any alcohol that is formed. The ketone can be added in pure form or in solution, alone or with a portion of the ester which is not in the starting mixture.

The ester may be used in simple form, or as a partial or complete self-condensate. According to one embodiment of the invention, if the ester has at least one hydrogen in a position alpha to the ester group, it may be employed at least partly in the form of the β-ketoester derived from it, or in the form of one of its salts. For example, if the formula of $R_6$ is written as $$(R'_6)(R''_6)CH—,$$

the β-ketoester is then written as $$R_6C(O)(R'_6)(R''_6)CC(O)OR_7,$$

where $R'_6$ and $R''_6$ may each be hydrogen or a hydrocarbon group. This unexpected result completely contradicts the teachings of the relevant art, and enables the use of conditions that favor formation of β-ketoester, since addition of the ketone under the proper operating conditions provides the β-diketone(s) desired.

The alcoholate may be any alcoholate the alcohol of which is volatile under reaction conditions, and is preferably an alkali metal or alkaline earth metal alcoholate. More preferably, the alcoholate is an alkali metal or alkaline earth metal alkoxide. Particularly preferred alcoholate are alkali metal alkoxides having from 1 to 4 carbon atoms. Most preferably, the alcoholate is sodium methylate (methoxide).

During the addition of the ketone, any alcohol that is formed is removed, preferably by distillation while refluxing the solvent. Accordingly, the reaction temperature is preferably at least 20° C. greater than the boiling point of the alcohol. More preferably, the reaction temperature is at least 70° C., most preferably at least 100° C. In a particular preferred embodiment of the present invention, the reaction temperature ranges from 100° to 200° C., and more preferably from 110° to 150° C., at atmospheric pressure.

Pressure is not critical to the present method, except to the extent that the selection of a particular pressure may facilitate rapid removal of the alcohols released in the reaction medium. If the reaction occurs at reduced pressure, the preferred reaction temperature ranges from 80° to 150° C.

Preferably, the molar ratio of the ketone to the ester is less than 1, more preferably between ⅔ and 1. Generally, a 10 to 20% excess of ester is used in relation to the ketone.

Preferably, the stoichiometric molar ratio of the ketone to the alcoholate is less than 1, more preferably between ⅔ and 1. Generally, a 5 to 25% excess of the alcoholate is used in relation to the ketone.

The solvent, which may be a pure substance or a mixture, is preferably selected to have a high boiling point at atmospheric pressure so that the alcohol released by the various reactions may be removed without removal of the solvent. Accordingly, it is preferred that at atmospheric pressure the solvent has a boiling point ranging from 100+ to 250° C., more preferably from 110° to 200° C. Most preferably, the solvent has a boiling point from 130° to 200° C.

For good separation of the solvent from the alcohol, the boiling point of the solvent is preferably at least 20° C. above that of the alcohol, more preferably at least 40° C. above, and most preferably at least 60° C. above. Alternatively, the solvent may contain, as a minor component, a substance that forms a minimum azeotrope with the alcohol; it is preferred that the boiling point of this azeotrope be sufficiently distant from that of the reaction mixture so that it (the azeotrope) can be easily separated from the solvent in the reflux.

The same constraints that apply to the alcohol of the alcoholate apply to the alcohol of the ester, mutatis mutandis. Thus, with the ester alcohol, the solvent also preferably has a boiling point at least 20° C. above that of the alcohol $R_7OH$, more preferably at least 40° C. above, and most preferably at least 60° C. above.

If the solvents which are used boil at a temperature higher than that at which the routineer wants to conduct the reaction, removal of the alcohols may be facilitated by any suitable technique known to the art, such as bubbling an inert gas or working under reduced pressure.

If the solvent is comprised of a single principal constituent, it is preferred to select a solvent that does not form an azeotrope with the alcohol formed, and thus avoid a situation whereby the alcohol is reintroduced to the reaction mixture when the azeotrope undergoes reflux. In the alternative, it is possible to remove the alcohol-containing azeotrope progressively as it is released.

The rate of addition of the ketone is selected such that the alcohol content in the reaction medium is kept as low as possible, preferably such that during the addition, the ratio between the alcoholate and free alcohol in solution is preferably at least about $10^3$:1, more preferably $10^6$:1, most preferably $10^9$:1. If the reaction temperature is below 70° C., it is preferable to reduce the rate of addition by dividing, for example, by a factor of 2.

Particularly preferred embodiments of the present method are a rate of addition of at most 0.001 mole ketone per second per liter of alcoholate suspension in the starting reaction mixture, which can yield good results, and a rate of at most 0.0002 mole/second/liter, which can yield excellent results.

A third embodiment of the present invention is directed to β-diketones formed by the inventive method described above.

A fourth embodiment of the present invention is directed to halogenated polymers containing the stabilizing composition described above. Halogenated polymers, such as PVC, are generally known to the art as are methods for incorporating stabilizing compositions. Any amount of the stabilizing composition effective to stabilize the halogenated polymer may be used, and it is within the skill of the art to determine particularly preferred amounts based on the desired application.

The following examples are merely illustrative of the invention and should not be construed as limiting. One skilled in the art can make, without undue experimentation, various substitutions and variations and by equivalent means, performing in substantially the same manner, obtain substantially the same results without departing from the teaching and spirit of the invention.

Example 1

Study of the Physico-Chemical Properties of the β-diketones:

TABLE 1

| Substance: | Vapor pressure at 180° C. (mmHg) (Pa) | Physical state | Odor |
|---|---|---|---|
| Heptanoylacetophenone | 7 | Liquid, m.p. melting point 11° C. | Very faint |
| Octanoylacetophenone | 5.6 | Solid, m.p. 33° C. | Very faint |
| Isooctanoylacetophenone | 6 | Liquid | Very faint |
| Isononanoylacetophenone | 4 | Liquid | Very faint |
| Isodecanoylacetophenone | 2 | Liquid | Very faint |
| Isoundecanoylacetophenone | 1.5 | Liquid | Very faint |
| Isovaleroylacetophenone (comparative) | 28 | Liquid | Strong |
| Dibenzoylmethane (comparative) | 4 | Solid, m.p. 78° C. | Slight |

It is seen from Table 1 that the two comparative examples at the bottom of the table must be rejected.

| Substance | Solubility in dioctyl phthalate, "DOP" g/100 g solvent | | | Solubility in "one-pack" additive, g/100 g solvent: | | |
|---|---|---|---|---|---|---|
| | 23° C. | 3° C. | −15° C. | 23° C. | 3° C. | −15° C. |
| Heptanoylacetophenone | >100 | >100 | 50–100 | >18 | >18 | >18 |
| Octanoylacetophenone | >100 | 50–100 | 12–25 | >18 | >18 | 9–18 |
| Isooctanoylacetophenone | Miscible in all proportions | | | Miscible in all proportions | | |
| Isononanoylacetophenone | Miscible in all proportions | | | Miscible in all proportions | | |
| Isodecanoylacetophenone | Miscible in all proportions | | | Miscible in all proportions | | |
| Isoundecanoylacetophenone | Miscible in all proportions | | | Miscible in all proportions | | |
| Isovaleroylacetophenone (comparative) | Miscible in all proportions | | | Miscible in all proportions | | |
| Dibenzoylmethane (comparative) | 10–20 | about 10 | 5–10 | about 9 | 5–9 | <5 |

Table 1 gives the vapor pressures at 180° C., which is a typical temperature at which PVC is employed.

Branched β-diketones solve the problem posed quite well, but the linear β-diketones, despite having melting points close to ambient temperature (9°–33° C.), are at least as satisfactory, as will be seen infra, because they have good solubility in dioctyl phthalate "DOP", (a classic plasticizer for PVC) and in the "all in one" or "one-pack" liquid stabilizing formulation.

Example 2

Solubilities of the Inventive Compounds

2.1. Solubilities in the Customary Solvents

The inventive mixture designated OBM herebelow has a diketone component with the following composition:

| Octanoyl benzoylmethane | 80% |
|---|---|
| Dibenzoylmethane | 6% |
| Dioctanoylmethane | 4% |
| Hexanoyl benzoylmethane | 6% |
| Dihexanoylmethane | 0.3% |

Various inert impurities account for 3.5%.

Above 20° C., OBM is completely miscible with most common solvents. Its solubility is more limited at low temperatures, as indicated in the following table:

TABLE 2

| Solvent: | Solubility (g/100 g solvent), at various temperatures: | | |
|---|---|---|---|
| | 22° C. | 5° C. | −10° C. |
| Hexane | >100 | >100 | −15 |
| Toluene | >100 | >100 | −15 |
| Ethyl acetate | >100 | >100 | 50–100 |
| Acetone | >100 | >100 | 25–50 |
| Dichloromethane | >100 | >100 | 50–100 |
| Ethanol | >100 | <20 | low |

These examples may be regarded as a test of the solubility of the compositions according to the invention, but not as being conclusive as to the particular data. Solvents should be avoided in the "all in one" formulations.

2.2. Solubilities in Dioctyl Phthalate (DOP)

Direct observation of melting points is disturbed by supersaturation phenomena. To eliminate this effect, two methods are used for the same mixtures:

Melting Point by Direct Observation

Various mixtures of OBM and DOP were stored 4 days at one of the temperatures given (22° C. 5° C. and −15° C.), following which the melting point was observed (see Table 3, infra) (S=soluble, I=insoluble).

Melting Point by Differential Thermal Analysis (DTA)

Two points were determined:
temperature of initiation of solubilization peak (initiation of melting); and
temperature of the maximum of the peak.
Assuming the actual temperature of solubilization to be 4° C. above the temperature of initiation of the peak, one obtains the curve of solubilization of OBM in DOP. The mixture according to the invention designated by OBM is made by the process of Example 9 and is constituted in the diketone fraction by:

| Octanoyl benzoylmethane | 80% |
|---|---|
| Dibenzoylmethane | 6% |
| Dioctanoylmethane | 4% |
| Hexanoyl benzoylmethane | 6% |
| Dihexanoylmethane | 0.3% |

Various inert impurities account for 3.5%.

TABLE 3

| Mixture | | Solubilities observed | | | Fusion point by DTA | | Temperature of |
|---|---|---|---|---|---|---|---|
| % OBM | % DOP | 22° C. | 5° C. | −15° C. | Initial | At Peak | solubility |
| 100 | 0 | Limited | I | I | 17.6°C. | 28° C. | 22° C. |
| 95 | 5 | S | I | I | 14.2 | 29.1 | 19 |
| 90 | 10 | S | I | I | 13.9 | 27.9 | 18 |
| 85 | 15 | S | I | I | 12.3 | 25.2 | 16 |
| 80 | 20 | S | I | I | 10.3 | 21.2 | 14 |
| 70 | 30 | S | I | I | 9.6 | 22.7 | 13 |
| 60 | 40 | S | I | I | 4.4 | 18.7 | 8 |
| 50 | 50 | S | S | I | 0.2 | 14.8 | 4 |
| 40 | 60 | S | S | I | −4.4 | 10.9 | 0 |
| 30 | 70 | S | S | I | −7.7 | +5.7 | −3 |
| 20 | 80 | S | S | I | — | — | |
| 10 | 90 | S | S | S | — | — | <−15 |

KEY: S = soluble, I = insoluble.

Example 3

Solubility in the Principal Constituents of an "All In One" Additive

The purpose was to compare the behavior of a mixture based on a composition according to the invention with a mixture based on dibenzoylmethane, in preparing a mixture of stabilizing agents.

Methodology

The mixtures were weighed in screw-capped bottles.
The bottles were placed in a shaking machine for agitation, for several hours.

TABLE 4

| Observations | | | | | |
|---|---|---|---|---|---|
| Formulations | | | | Results | |
| Ba | Zn | Phosphite | β-diketone | OBM | Dibenzoyl methane |
| 0 | 2/3 | 0 | 1/3 | S | I |
| 0 | 0 | 1/3 | 2/3 | S | I |
| 0 | 0 | 2/3 | 1/3 | S | I |
| 0 | 1/2 | 0 | 1/2 | S1 | I |
| 0 | 0 | 1/2 | 1/2 | S | I |
| 1/4 | 1/4 | 1/4 | 1/4 | S2 | I |

TABLE 4-continued

| | | Formulations | | Observations | Results |
|---|---|---|---|---|---|
| Ba | Zn | Phosphite | β-diketone | OBM | Dibenzoyl methane |
| 1/8 | 1/8 | 3/8 | 3/8 | S | I |
| 1/10 | 3/10 | 3/10 | 3/10 | S | I |
| 1/10 | 2/10 | 5/10 | 2/10 | S | I |
| 1/10 | 3/10 | 0 | 6/10 | S | I |

KEY:
Ba = Barium p-tert-butylbenzoate.
Zn = Zinc octoate.
Phosphite = Diphenyl isodecyl phosphite (an alkyl aryl phosphite).
β-diketone = OBM or dibenzoylmethane.
S = Mixture soluble.
S1 = Mixture soluble but viscous.
S2 = Mixture soluble but very viscous.
I = Mixture insoluble.

Comparative Example 4

Solubility of a Diketone Used Currently, Viz., Dibenzoylmethane: In Formula (I), R1=R2=Phenyl.

TABLE 5

| | Solubility (q/100 g solution) | | |
|---|---|---|---|
| Solvent | at 25° C. | at 3° C. | at −15° C. |
| Epoxidized soy oil, ESO | 10–20 | 10–20?(1) | <1 |
| Dioctyl phthalate, DOP | 10–20 | — | 5–10 |
| Dioctyl adipate, DOA | 20–30 | 10–20 | 5–10 |
| Octyl trimellitate, OTM | 10–20 | — | 5–10 |
| Trilauryl phosphite(2), "OS 360" | <10 | — | — |
| Tridecyl phosphite(2), "OS 330" | <10 | — | — |
| Phenyl didecyl phosphite(2), "OS 300" | 10–20 | 10–20 | <10 |
| Diphenyl decyl phosphite(2), "OS 150" | <10 | — | — |
| Phosphite of butylcarbitol and bisphenol A(2) | 10–20 | 10–20 | about 10 |
| Tetralin | 20–30 | 10–20 | <10 |
| Decalin | 5–10 | <5 | — |

Footnotes to Table 5:
(1)This value is probably high (crystallization was slow, taking >1 mo.
(2)For the phosphites, only 10% and 20% solutions were examined.

These results may be compared with those for isooctanoylacetophenone (according to the present invention), which at the same temperature, is soluble in all proportions with the solvents named above.

Example 5

Synthesis of Heptanoyl-Benzoylmethane

To a 2000 ml Pyrex round-bottomed flask, the following were charged:

| | |
|---|---|
| Sodium methylate, freshly prepared | 62.6 g (1.16 mol) |
| Xylene | 715 ml. |

The mixture was heated to 100° C., then the following was added over a period of approximately 10 min:

| | |
|---|---|
| Methyl heptanoate, pure | 158.4 g (1.10 mol). |

The reaction mixture was brought to reflux (about 137° C.), then the following was added gradually over 2 hr with stirring:

| | |
|---|---|
| Acetophenone, pure | 120.0 g (1.0 mol). |

During all of these steps, the reaction mixture was maintained under an inert nitrogen atmosphere, and a xylene-methanol mixture was distilled off such that the temperature T (°C.) of the vapors distilled off at the head of the column which had a "multiknit" knit cover varied within the range 108°–115° C. The distilled mixture was recovered in a round bottomed receiving flask.

The amount of solvent in the reaction medium was kept generally constant at about 715 ml by supplemental addition of xylene.

The reaction medium remained fluid and homogeneous during the entire process.

At the conclusion of the addition of the acetophenone, reflux was continued 1 hr, during which an additional small quantity of methanol was distilled off. Over the entire operation, the mixture distilled comprised 140 g xylene and 62 g methanol. The mixture was allowed to cool, then was transferred under agitation to a 2000 ml beaker containing 800 g ice and 38.6 ml 95% sulfuric acid (comprising about 0.7 mol $H_2SO_4$). The aqueous phase was decanted into a decanting ampoule, and was then washed with 2×100 ml xylene. The washing xylene was then combined with the organic phase, which was then washed with 2×250 ml water, dried over anhydrous sodium sulfate, and filtered.

In this way, 1014 g of a solution in xylene was obtained, in which a content of 0.870 mol β-diketone was determined by potentiometry; this represented a chemical yield of β-diketone of 87%, on the basis of the ketone charged. Also, 0.170 mol carboxylic acid was determined by potentiometry.

After extraction of the carboxylic acids by a stoichiometric amount of aqueous sodium hydroxide (or sodium carbonate), and removal of the xylene under reduced pressure, 217 g of a raw product in the form of a homogeneous oil was obtained.

Gas chromatographic analysis (GC) of this product showed that it contained three β-diketones (usable as a mixture in the stabilization of halogenated polymers), as follows:

| | |
|---|---|
| Heptanoylbenzoylmethane | 182 g (83.9%) |
| Dibenzoylmethane | 11.2 g (5.1%) |
| Diheptanoylmethane | 8.6 g (4.0%). |

This analysis confirms the overall chemical yield of 87% (based on the ketone charged).

Distillation of this reaction mixture was easy to accomplish, and resulted (with yield of about 96%) in a mixture of the three β-diketones having purity of about 99%.

Distillation was also used to isolate pure heptanoylbenzoylmethane, with good yield (about 90%). This product was present in the form of a colorless oil with boiling point 112°–115° C. (at 1 Torr). Its melting point was 14° C., its refractive index at 30° C. was 1.5558, and its density at 30° C. was 1.004. NMR analysis showed that it comprised 90% enolic form and 10% diketone form.

Example 6

Heptanoylbenzoylmethane

The procedure was as in Example 5, with the only difference being that only 144 g (1 mol) methyl heptanoate was added.

The potentiometric analysis and the GC analysis of the final solution in xylene showed that the yield of β-diketones was 81.1% (based on the ketone charged).

Example 7

Heptanoylbenzoylmethane (Comparison Example)

The procedure was as in Example 5, with the only difference being that 316.8 g (2.2 mol) methyl heptanoate was added.

The potentiometric analysis and the GC analysis of the final solution in xylene showed that the yield of β-diketones was 94.8% (based on the ketone charged).

The same analyses revealed that only 0.9 mol unconsumed ester remained; thus, the yield of β-diketones based on the ester consumed, viz. 72.9%, was appreciably lower than that obtained in Example 5, viz. 79.1% (assuming that all of the ester in Example 5 was consumed).

Thus, the use of a large excess of the ester carries with it two major disadvantages:

The ester is recycled; and

The yield of β-diketones (based on the amount of ester consumed) is appreciably lower (which can be explained by formation of by-products).

Example 8

Octanoylbenzoylmethane

The following were charged to the reactor described in Example 5:

| | |
|---|---|
| Sodium methylate, freshly prepared | 62.6 g (1.16 mol) |
| Xylene | 715 ml. |

The mixture was heated to 100° C. under a dry nitrogen atmosphere, then the following was added over a period of about 10 min:

| | |
|---|---|
| Methyl octanoate, pure | 173.8 g (1.10 mol). |

The reaction mixture was brought to reflux (about 137° C.), then the following was added gradually over 2 hr with stirring:

| | |
|---|---|
| Acetophenone, pure | 120.0 g. (1.0 mol). |

The subsequent steps were the same as described in Example 5.

The mixture of xylene and methanol which was distilled off weighed 203 g (comprised of about 140 g xylene and about 63 g methanol).

1033.3 g of a solution in xylene was recovered, in which 0.871 mol β-diketones was determined by potentiometry (representing a chemical yield of β-diketones of 87.1% with respect to the ketone charged). 0.170 mol carboxylic acids was also determined by potentiometry.

After extraction of the carboxylic acids by a stoichiometric amount of aqueous sodium hydroxide (or sodium carbonate), and removal of the xylene under reduced pressure, 228 g of a raw product in the form of a yellow oil which was fluid and homogenous was obtained.

Gas chromatographic analysis (GC) of this product showed that it contained three β-diketones, as follows:

| | |
|---|---|
| Octanoylbenzoylmethane | 190.9 g (83.7%) |
| Dibenzoylmethane | 12.4 g (5.4%) |
| Dioctanoylmethane | 10.8 g (4.7%). |

This analysis confirms the overall chemical yield of 87% (based on the ketone charged).

Distillation of this reaction mixture was easy to accomplish, and resulted in separation of the β-diketones (about 94%) from the tars (about 6%). The yield of the distillation was about 97%, and the product obtained analyzed for β-diketones in the amount of >99%.

Isolation of pure octanoylbenzoylmethane was achieved in good yield (about 85%) by careful distillation. This product was obtained in the form of a white solid with a low melting point (about 34° C.) and a boiling point of 121°–122° C. (at 0.1 Torr). Its index of refraction (30° C.) was 1.5445, and its density at 30° C. was 0.982. NMR analysis showed that it comprised 91% enolic form and 9% diketone form.

Example 9

Octanoylbenzoylmethane

The following were charged to the reactor described in Example 5:

| | |
|---|---|
| Sodium methylate, freshly prepared | 62.6 g (1.16 mol) |
| Xylene, dry | 150 ml. |

The mixture was heated to 100° C. under a dry nitrogen atmosphere, then the following was added over a period of about 10 min:

| | |
|---|---|
| Methyl octanoate, containing 6.8% methyl hexanoate | 189.9 g (1.20 mol). |

The reaction mixture was brought to reflux (about 137° C.), then the following was added gradually over 2 hr with stirring:

| | |
|---|---|
| Acetophenone, pure | 120.0 g. (1.0 mol). |

The subsequent steps were the same as described in Example 5, except that the reaction mixture was acidified with 69 g H₂SO₄ (0.67 mol) and washed with 100 ml xylene.

Gas chromatographic analysis (GC) of this product, which melted at about 24° C., showed that it contained five β-diketones, as follows:

| | |
|---|---|
| Octanoylbenzoylmethane | 80% |
| Dibenzoylmethane | 6% |
| Dioctanoylmethane | 4%. |
| Hexanoylbenzoylmethane | 6% |
| Dihexanoylmethane | 0.3%. |

The composition also contained about 3.7% impurities.

Examples 10–16

The procedure was the same as in Example 8, but certain parameters of the reaction were changed, viz.:

the ratios of the reactants (excess ester, and excess MeONa); and the duration of the period of addition of the acetophenone.

The results obtained (overall chemical yield of β-diketones) are given in Table 6 (in comparison with Example 8).

TABLE 6

Example Parameters Modified:

| Number: | Duration of addition of ΦCOCH3: | Ester fed: | MeONa fed: | Yield of β-diketones (based on ΦCOCH3): |
|---|---|---|---|---|
| 8 | 2 hr | 1.1 mol | 1.16 mol | 87.1% |
| 10 | 2 hr | 1.0 mol | 1.16 mol | 80.0% |
| 11 | 2 hr | 1.175 mol | 1.16 mol | 88.7% |
| 12 | 7 hr | 1.175 mol | 1.16 mol | 88.4% |
| 13 | 1 hr | 1.175 mol | 1.16 mol | 82.7% |
| 14 | 2 hr | 1.175 mol | 1.025 mol | 88.5% |
| 15 | 2 hr | 1.175 mol | 1.075 mol | 89.5% |
| 16 | 2 hr | 1.22 mol | 1.16 mol | 88.9% |

These results demonstrate the following:

The effect of excess ester is very marked when the excess goes from 0% to 10%.

The effect of excess methylate is very small.

The effect of the duration of addition: Addition times of 2 hr and 7 hr give essentially the same result. However, too rapid addition (duration 1 hr) can have a substantial detrimental effect on the result; this is attributed to insufficiently rapid removal of the methanol with respect to the rate of formation of methanol. (It is very important that the ratio of MeOH to MeO be >1,000.)

Example 17

Synthesis of Methyl Octanoyloctanoate

The following were charged to the reactor described in Example 5:

| | |
|---|---|
| Sodium methylate, freshly prepared | 54.0 g (1.0 mol) |
| Xylene | 715 ml. |

The mixture was heated to 100° C., then the following was added over a period of about 10 min:

| | |
|---|---|
| Methyl octanoate, pure | 316.0 g (2.0 mol). |

The reaction mixture was brought to reflux (about 140° C.), with the methanol being distilled off progressively as it was formed.

It was found that the methanol formed slowly.

After 7.5 hr of reflux and continuous removal of methanol, the amount of methanol which had been distilled off was about 46 g, in a mixture with about 10 g xylene. The operation was concluded.

After acidification of the reaction mixture as in Example 5, 1006.8 g of a clear yellow solution in xylene was obtained, in which 0.16 mol carboxylic acid was determined, by potentiometry. After removal of these carboxylic acids by the necessary stoichiometric amount of aqueous sodium hydroxide (or sodium carbonate), 0.520 mole of residual ester was determined, by GC (the TT of the ester was 74%). After removal of the xylene at reduced pressure, 206.3 g of a raw product was obtained in the form of an oily homogenous fluid with a faint yellow color.

Distillation of this raw product led to 135 g of a pure product having boiling point 123°–124° C. (at 0.25 Torr). This product was in the form of a colorless, fluid oil.

Analyses and IR and NMR and MS spectra were in agreement with the structure of the following β-ketoester product, with purity > 99%:

C₇H₁₅COC(C₆H₁₃)HC(O)OMe (M=284)

The yield of pure distilled β-ketoester (0.475 mole) (based on the amount of ester converted, 1.48 mole) was 64%.

Example 18

Octanoylbenzoylmethane from the β-ketoester

The apparatus was the same as described in Example 5, but the reactor size was only 1 L.

The following were charged into the reactor:

| | |
|---|---|
| Sodium methylate, freshly prepared | 43.2 g (0.8 mol) |
| Xylene | 475 ml. |

The mixture was heated to 140° C., then the following β-ketoester was added slowly, while carefully and thoroughly removing the methanol formed:

| | |
|---|---|
| Methyl octanoyloctanoate | 113.8 g (0.4 mol). |

The duration of addition was 1 hr 20 min. At the conclusion of the addition, the β-ketoester was found to be quantitatively in the form of the sodium enolate.

The temperature was maintained at 140° C., and the following was added gradually over a period of 2 hr, while carefully and thoroughly removing the methanol formed:

| | |
|---|---|
| Acetophenone | 80.5 g (0.67 mol). |

At the conclusion of the addition of the acetophenone, the mixture was maintained another 30 min at 140° C. At this stage, a mixture of xylene and methanol weighing about 140 g had been distilled off, which comprised about 112 g xylene and about 28 g methanol.

Comment: As in Example 5, all of the steps were carried out under an inert nitrogen atmosphere, and make-up xylene was added to maintain an essentially constant total amount of solvent in the reaction mixture.

At the end of the operation, the reaction mixture was cooled and transferred under agitation to a beaker containing 500 g ice and 28 ml 95% sulfuric acid (comprising about 0.7 mol $H_2SO_4$). The organic phase was then separated from the aqueous phase as in Example 5.

675.5 g of a solution in xylene was recovered, in which 0.583 mol of β-diketone function was determined by potentiometry, for a chemical yield of β-diketones of 87% (based on the ketone charged). (The β-ketoester, which was too non-acidic, did not interfere with the determination by potentiometry in the aqueous medium.) Also by potentiometry, 0.0965 mol carboxylic acid was determined. The following were determined in the reaction mixture, by GC analysis:

| | |
|---|---|
| Residual β-ketoester | 0.011 mol |
| (This is 2.8%, based on the β-ketoester charged.) | |
| Methyl octanoate | 0.037 mol |
| (This is 4.6%, based on the β-ketoester charged.) | |

Also the β-diketone mixture was determined to have the following components:

| | |
|---|---|
| Octanoylbenzoylmethane | 0.546 mol |
| (This is 81.5%, based on the ketone charged.) | |
| Dibenzoylmethane | 0.22 mol |
| (This is 3.3%, based on the ketone charged.) | |
| Dioctanoylmethane | 0.015 mol |
| (This is 2.2%, based on the ketone charged.) | |

After removal of the solvent, such a reaction mixture could be used directly for stabilization of halogenated polymers such as polyvinyl chloride (PVC).

Example 19

Synthesis of Dibenzoylmethane

Into a cylindrical 2000 ml reactor equipped with
an agitator having scraper blades and
a distillation system as described in Example 5, the following were charged:

| | |
|---|---|
| Sodium methylate, freshly prepared | 67.5 g (1.15 mol) |
| Xylene | 800 ml. |

The mixture was heated to 135° C., then the following was added rapidly (over a period of 5 min):

| | |
|---|---|
| Methyl benzoate (98.5%) | 151.8 g (1.10 mol) |

The medium was brought to reflux, and then the following was introduced over a period of 4 hr, with the temperature of 135° C. being maintained:

| | |
|---|---|
| Acetophenone | 120 g (1 mol). |

The reaction medium was maintained at reflux for 30 min after conclusion of the addition of the acetophenone, and collection of the distillate was continued (vapor temperature 70° C.). A total of 130 ml distillate was collected.

The medium was thick, but remained capable of being stirred.

The medium was then neutralized by a solution of 10% sulfuric acid. After decantation and washing operations, 881 g of a solution of dibenzoylmethane in xylene was obtained which analyzed at 1.057 mol/kg, for a yield of 93.1% (based on the ketone).

Example 20

Synthesis of Stearoylbenzoylmethane and Palmitoylbenzoylmethane

The following were charged into an apparatus similar to that of the preceding Examples:

| | |
|---|---|
| Sodium methylate, freshly prepared | 67.5 g (1.15 mol) |
| Toluene | 1000 ml. |

The mixture was heated to 105° C., then the following was added rapidly:

| | |
|---|---|
| Methyl stearate, technical (containing other fatty acid esters, particularly methyl palmitate in the amount of 33%) | 293 g (1.03 mol). |

The medium was brought to reflux, and then the following was introduced over a period of 2 hr:

| | |
|---|---|
| Acetophenone | 120 g (1.0 mol) |

The mixture was allowed to reflux for 30 min after the addition of the acetophenone. During the entire reaction, the toluene-methanol azeotrope containing substantial toluene was collected continuously (vapor temperature 90° C.); the volume collected was 390 ml. The medium at completion of the reaction was homogenous. It was acidified to bring the pH to 1. After washing, 993 g of a solution in toluene of a mixture of β-diketones which analyzed at 0.863 mol/kg was obtained, giving a yield of 85.7% (on the basis of the ketone charged).

After removal of the solvent, such a reaction mixture was directly usable for stabilization of halogenated polymers (such as PVC).

Example 21

Palmitoylbenzoylmethane

The apparatus and method were as described in Example 1, but with the following starting materials:

| Sodium methylate, freshly prepared | 59.4 g (1.1 mol) |
|---|---|
| Xylene | 715 ml. |
| Methyl palmitate, pure ($C_{15}H_{31}C(O)OMe$, m.w. 270.5) | 324.6 g (1.2 mol) |
| Acetophenone, pure | 120.0 g (1.0 mol). |

(NB: Palmitoyl-benzoylmethane, $C_{15}H_{31}COCH_2CO\Phi$, has molecular weight 358.6.)

The operations and the method were identical to those described in Example 5. The distillation product collected comprised 150 g xylene and 62 g methanol.

The xylene phase was washed and dried, and was then "devolatilized" (freed of volatile components) to remove the xylene. (A rotary evaporator was used, with pressure reduced to 15 Torr and temperature 110° C. at the conclusion of the operation.)

405.6 g raw product was recovered, in the form of a clear yellow solid with melting point 56°–60° C., containing (by GC analysis)

| Palmitoylbenzoylmethane, m.w. 358.6 | 290.5 g (0.81 mol) |
|---|---|
| Dipalmitoylmethane, m.w. 492 | 16.3 g (0.033 mol) |
| Dibenzoylmethane, m.w. 224 | 9.0 g (0.04 mol). |

The overall yield of β-diketones was thus 0.873 mol, which was 87.3% (on the basis of the ketone charged).

The content of β-diketones in the raw product was 77.9%.

Recrystallization of the raw product out of a cold 50:50 mixture of acetone and methanol resulted in recovery of 292 g of an odorless white product having melting point 62°–64° C., comprised solely of a mixture of the following two β-diketones:

| Palmitoylbenzoylmethane | 276 g (94.5% of the cold material) |
|---|---|
| Dipalmitoylmethane | 16 g (5.5% of the cold material). |

The crystallization yield was about 95%.

Example 22

Stearoylbenzoylmethane ($C_{17}H_{35}COCH_2CO\Phi$, from $C_{17}H_{35}C(O)OMe$):

The method was as in Example 5, using the following starting materials:

| Sodium methylate, freshly prepared | 59.4 g (1.1 mol) |
|---|---|
| Xylene | 715 ml. |
| Methyl stearate, pure ($C_{17}H_{35}CO(O)Me$) | 328.4 g (1.1 mol) |
| Acetophenone, pure | 120.05 g (1 mol). |

414.5 g of a raw product was obtained in the form of a clear yellow solid having a melting point of 58°–65° C. GC analysis showed that this product contained the following:

| Stearoylbenzoylmethane, m.w. 386.3 | 304 g (0.787 mol) |
|---|---|
| Distearoylmethane, m.w. 548 | 13.7 g (0.025 mol) |
| Dibenzoylmethane, m.w. 224 | 7.9 g (0.035 mol) |
| TOTAL of β-diketones | 325.6 g (0.847 mol) |

The overall chemical yield of β-diketones was thus 84.7% (0.847 mol).

The content of β-diketones in the raw product obtained was 78.5%.

Recrystallization of this raw product from a cold 50:50 mixture of acetone and methanol resulted in recovery of 305 g of an odorless white product having melting point 67°–69° C., comprised solely of a mixture of the following two β-diketones:

| Stearoylbenzoylmethane | 291.8 g (95.7%) |
|---|---|
| Dipalmitoylmethane | 13.2 g (4.3%). |

The yield of the crystallization was about 96%.

Comment: The method described in Example 10 of U.S. Pat. No. 5,015,777, which employs a large excess of ester (4 times theoretical), gave a yield of only 45% (of a 95% pure product). We used only a 10% excess of ester, and obtained a chemical yield of 84.7% and a yield after crystallization of about 80%.

After removal of the solvent, such a reaction mixture could be used directly for stabilization of halogenated polymers (such as PVC).

Example 23

Octanoylbenzoylmethane: Effect of the operating technique—simultaneous addition of the two reactants (ester and ketone):

To determine the effect of at least partially simultaneous addition of the ketone and the ester, the following two tests were carried out, using the apparatus and procedure described in Example 5.

TABLE

Test type:
Starting materials (mol):

Supplemental

|  | Initial charges: | | | additions (2): | | |
|---|---|---|---|---|---|---|
|  | Ester (1) | MeONa | Xylene | ΦCOCH$_3$ | Ester | Yield: |
| A) Control | 1.20 | 1.10 | 715 ml | 1 | — | 89.5% |
| B) Test with simultaneous addition | 0.200 | 1.10 | 715 ml | 1.00 | 1.00 | 79.7% |

(1) Methyl octanoate.
(2) Addition over a period of 2 hr. Test A: Addition of only ΦCOCH$_3$. Test B: Addition of a mixture of ΦCOCH$_3$ and ester.

The determinations were carried out by potentiometry.

The progress over the state of the art is significant. In fact, it is about 10% better. In this method of operation, as shown in Test B, the continuous removal of MeOH is accomplished, but the excess of the ester is insufficient (even though a part, 20%, of the ester is introduced in the initial charge). With respect to Test A, it is no less advantageous to have at least 30% of the ester which is to be reacted be present in the initial charge of the reactor.

Example 24

Isooctanoylbenzoylmethane

The method was as in Example 5, but the reactants were as follows:

| Sodium methylate, freshly prepared | 62.6 g (1.16 mol) |
|---|---|
| Xylene | 715 ml. |
| Methyl isooctanoate, 99% (1) | 192 g (1.20 mol) |
| Acetophenone, 100% | 120 g (1.0 mol). |

The methyl isooctanoate was comprised mostly of methyl 3,5-dimethylhexanoate, CH$_3$CH(CH$_3$)CH$_2$CH(CH$_3$)C(O)OCH$_3$.

The product was analyzed as 625 meq ester/100 g.

After acidification of the reaction mixture by H2SO$_4$, washing, etc., 941.4 g of a solution in xylene was obtained.

After removal of the xylene, 262 g of a raw product was obtained, in the form of a homogenous yellow oil.

This product was determined to comprise the following, by potentiometry:

| β-diketone functions | 0.684 mol |
|---|---|
| Carboxylic acid functions | 0.327 mol. |

Comment: The overall chemical yield of β-diketones was 68.4%. This is appreciably lower than obtained with the ester of a C$_8$ linear acid (viz., 88.7%—see Example 11, under the same conditions). This is not surprising because the branched esters, which are less reactive than the linear esters with respect to titres of ΦCOCH$_2$, produce more heavy by-products.

Example 25

Hexanoyloctanoylmethane, C$_5$H$_{11}$COCH$_2$COC$_7$H$_{15}$

The method was as in Example 5, but the reactants were as follows:

| Sodium methylate, freshly prepared | 59.4 g (1.10 mol) |
|---|---|

-continued

| Xylene | 715 ml. |
|---|---|
| Methyl octanoate (linear), 100% | 189.9 g (1.2 mol) |
| 2-Heptanone, 100% | 114.2 g (1.0 mol). |

After acidification of the reaction mixture by H$_2$SO$_4$, washing, etc., 1069.6 g of a solution in xylene was obtained, of a dark orange color, determined to contain the following, by potentiometry: 0.771 mol β-diketones and 0.206 mol carboxylic acids.

The overall chemical yield of the β-diketone functions was thus 77.1%. This is appreciably lower than that obtained starting with methyl octanoate and acetophenone, under the same conditions (e.g., Example 15 gave a yield 89.5% under very similar conditions).

The aliphatic methylketones, such as 2-heptanone, are thus less selective than acetophenone (have a greater tendency to crotonization). Analysis by GC of the mixture of β-diketones showed it to be comprised of three β-diketones with the following distribution by weight:

| Dihexanoylmethane | about 3.5% |
|---|---|
| Hexanoyloctanoylmethane | 92% |
| Dioctanoylmethane | 4.5%. |

After removal of the solvent, such a reaction mixture was directly usable for stabilization of halogenated polymers (such as PVC).

Example 26

Octanoylbenzoylmethane: Effect of operating method—reaction under reduced pressure The objective was to determine the influence of pressure and to verify the possibility of operating under reduced pressure; the procedure was as described in Example 8.

TABLE

| | Test type: | Operating conditions: | | | |
|---|---|---|---|---|---|
| | Duration of addition: | Temperature Φ | Solvent: | Pressure (Torr): | Yield: |
| Control | 2 hr | 138° C. | Xylene | 760 | 88.7% |
| Reduced Pressure (8/30 × 10$^5$ Pa) | 2 hr | 95° C. | Xylene | 200 | 91.6% |
| Reduced Pressure (4/30 × 10$^5$ Pa) | 2 hr | 77° C. | Xylene | 100 | 82.3% |
| Reduced Pressure (4/30 × | 5 hr | 77° C. | Xylene | 100 | 89.6% |

TABLE-continued

| | Test type: Operating conditions: | | | |
|---|---|---|---|---|
| Duration of addition: | Temperature Φ | Solvent: | Pressure (Torr): | Yield: |

10⁵ Pa)
Reduced
Pressure

These tests indicate that the reaction can be carried out at low temperature and reduced pressure. However, if the temperature is reduced to about 80° C. or below, it is preferable to add the ketone at a reduced rate of addition.

Although preferred embodiments of the invention are described herein in detail, it will be understood by those skilled in the art that variations may be made thereto without departing from the spirit of the invention or the scope of the appended claims.

We claim:

1. A substantially odor-free, non-toxic, liquid stabilizing composition for halogenated polymers comprising an amount effective to stabilize halogenated polymers of a mixture of at least two substantially odor-free, non-toxic, liquid β-diketone compounds represented by formula (I):

$$R_1COCH_2COR_2 \quad (I)$$

and/or formula (II)

$$R_2COCH_2COR_2 \quad (II)$$

wherein
$R_1$ is represented by the formula $$(Y)_n\text{-}\Phi\text{-},$$

wherein Φ is phenyl and each Y, which may be the same or different, is a hydrogen atom or a group selected from
hydrocarbon chains having 1 to 12 carbon atoms, alkoxy, silyl, and
nonreactive halogen atoms;
each $R_2$, which may be the same or different, is a hydrogen atom or a group selected from
hydrocarbon chains having 5 to 12 carbon atoms, aralkyl, or silyl; and n is an integer between 0 and 3;
with the proviso that if the number of carbon atoms in $R_2$ in formula (I) is less than 5, the sum of the carbons contained in the Y groups is at least 3 and at most 12, and that in formula (II), the total number of the carbon atoms in the two $R_2$s is at least 10.

2. The composition as claimed in claim 1, wherein (expressed in moles) at least ⅔ of the β-diketone compounds present in the composition correspond to formula (I) or formula (II), 3. The composition as claimed in claim 1, wherein (expressed in moles) at least ¾ of the β-diketone compounds present in the composition correspond to formula (I) or formula (II).

4. The composition as claimed in claim 1, wherein (expressed in moles) at least ⅘ of the β-diketone compounds present in the composition correspond to formula (I) or formula (II).

5. The composition as claimed in claim 1, wherein $R_2$ is an alkyl group and the sum of the carbons contained in Y is less than 6.

6. The composition as claimed in claim 1, wherein $R_2$ is an alkyl group and the sum of the carbon atoms contained in Y and $R_2$ is less than 12.

7. The composition as claimed in claim 1, wherein $R_2$ is an alkyl group and the number of carbon atoms in $R_2$ is between 5 and 9 if the chain is linear and between 5 and 12 if the chain is branched.

8. The composition as claimed in claim 1, wherein the composition further comprises at least one other β-diketone compound of formula (III)

$$R_1COCH_2COR_1 \quad (III)$$

wherein $R_1$ and $R_2$, which may be the same or different, are as defined in claim 1.

9. The composition as claimed in claim 1, wherein the composition further comprises at least one compound selected from the salts of zinc, the salts of alkaline earth metals, and the organic phosphites.

10. The composition as claimed in claim 9, wherein the ratio between the sum of the β-diketone compounds and the amount of said compound is at least 1:100.

11. The composition as claimed in claim 1, wherein said β-diketone is octanoylbenzoylmethane.

* * * * *